US012410473B2

(12) United States Patent
Baek et al.

(10) Patent No.: US 12,410,473 B2
(45) Date of Patent: Sep. 9, 2025

(54) ANALYTIC METHOD AND KIT FOR DIAGNOSING ALCOHOL USE DISORDERS

(71) Applicants: CHA UNIVERSITY INDUSTRY-ACADEMIC COOPERATION FOUNDATION, Pocheon-si (KR); SUNGKWANG MEDICAL FOUNDATION, Seoul (KR)

(72) Inventors: Kwang-Hyun Baek, Seoul (KR); Soo-Ji Kang, Goyang-si (KR)

(73) Assignees: CHA UNIVERSITY INDUSTRY-ACADEMIC COOPERATION FOUNDATION, Pocheon-si (KR); SUNGKWANG MEDICAL FOUNDATION, Seoul (KR)

( * ) Notice: Subject to any disclaimer, the term of this patent is extended or adjusted under 35 U.S.C. 154(b) by 990 days.

(21) Appl. No.: 17/285,370

(22) PCT Filed: Sep. 17, 2019

(86) PCT No.: PCT/KR2019/011952
§ 371 (c)(1),
(2) Date: Apr. 14, 2021

(87) PCT Pub. No.: WO2020/080683
PCT Pub. Date: Apr. 23, 2020

(65) Prior Publication Data
US 2021/0324475 A1    Oct. 21, 2021

(30) Foreign Application Priority Data

Oct. 18, 2018  (KR) .................. 10-2018-0124359

(51) Int. Cl.
*G01N 33/68* (2006.01)
*C12Q 1/6883* (2018.01)

(52) U.S. Cl.
CPC ....... *C12Q 1/6883* (2013.01); *G01N 33/6893* (2013.01); *C12Q 2600/158* (2013.01); *G01N 2333/912* (2013.01)

(58) Field of Classification Search
CPC ............ C12Q 1/6883; C12Q 2600/158; G01N 33/6893; G01N 33/573; G01N 2333/912; G01N 2333/9121; G01N 2800/02
See application file for complete search history.

(56) References Cited

U.S. PATENT DOCUMENTS

| 2006/0024658 | A1 | 2/2006 | Miles et al. | |
|---|---|---|---|---|
| 2010/0281583 | A1* | 11/2010 | Sutton | C07K 14/415 536/23.6 |
| 2012/0003639 | A1* | 1/2012 | Kerlikowske | C12Q 1/6883 435/7.1 |

OTHER PUBLICATIONS

Qin et al., "DC-CIK cells derived from ovarian cancer patient menstrual blood activate the TNFR1-ASK1-AIP1 pathway to kill autologous ovarian cancer stem cells," Journal of Cellular and Molecular Medicine, vol. 22, pp. 3364-3376. (Year: 2018).*
Boyacioglu et al., "Biological effects of tolerable level chronic boron intake on transcription factors," Journal of Trace Elements in Medicine and Biology, vol. 39, pp. 30-35. (Year: 2017).*
Huang et al., "Does lipopolysaccharide-mediated inflammation have a role in OA?," Nat Rev Rheumatol, vol. 12, No. 2, pp. 123-129. (Year: 2016).*
Overman et al., "Polyphenol-rich grape powder extract (GPE) attenuates inflammation in human macrophages and in human adipocytes exposed to macrophage-conditioned media," International Journal of Obesity, vol. 34, pp. 800-808. (Year: 2010).*
Liu et al., "ShRNA-Targeted MAP4K4 Inhibits Hepatocellular Carcinoma Growth," Human Cancer Biology, vol. 17, No. 4, pp. 710-720. (Year: 2011).*
Liu et al, Supplemental Information. (Year: 2011).*
Giovanelli et al., "Detection of JCPyV microRNA in blood and urine samples of multiple sclerosis patients under natalizumab therapy," J. Neurovirol, vol. 21, pp. 666-670. (Year: 2015).*
Yang et al., "Cytochrome P4502E1, oxidative stress, JNK, and autophagy in acute alcohol-induced fatty liver," Free Radical Biology and Medicine, vol. 53, pp. 1170-1180. (Year: 2012).*
Jovicic et al., "Modulation of c-Jun N-terminal kinase signaling and specific glucocorticoid receptor phosphorylation in the treatment of major depression," vol. 85, pp. 291-294. (Year: 2015).*
Shao et al., "Induction of apoptosis by Elk-1 and Elk-1 proteins," Oncogene, vol. 17, pp. 527-532. (Year: 1998).*
Medline Plus, "Alcohol Use Disorder (AUD) Treatment," Accessed via WayBack Machine. https://medlineplus.gov/alcoholusedisorderaudtreatment.html (Year: 2017).*
Besnard et al., "Elk-1 a transcription factor with multiple facets in the brain", Frontiers in Neuroscience, 2011, vol. 5, Article 35, pp. 1-11.
Pahng et al., "Dysregulation of c-Jun N-terminal kinase phosphorylation in alcohol dependence", Alcohol, 2019, vol. 75, pp. 11-18.

(Continued)

*Primary Examiner* — Angela M. Bertagna
*Assistant Examiner* — Francesca Filippa Giammona
(74) *Attorney, Agent, or Firm* — Vorys, Sater, Seymour and Pease LLP; Mih Suhn Koh

(57) ABSTRACT

Provided is an analytical method for providing information necessary for a diagnosis of alcohol use disorder, including measuring (i) an expression level of a gene encoding a JNK or p-JNK protein in a subject's sample, (ii) an expression level of a gene encoding a JNK or p-JNK protein and an expression level of a gene encoding the Elk-1 protein in a subject's sample, or (iii) expression levels of genes encoding JNK, p-JNK, and Elk-1 proteins in a subject's sample, respectively; and a kit for a diagnosis of alcohol use disorder which is used in the analytical method.

1 Claim, 2 Drawing Sheets

(56) References Cited

OTHER PUBLICATIONS

Pandey et al., "Effector Immediate-Early Gene Arc in the Amygdala Plays a Critical Role in Alcoholism", The Journal of Neuroscience, 2008, vol. 28, No. 10, pp. 2589-2600.
Warden et al., "Gene expression profiling in the human alcoholic brain", Neuropharmacology, 2017, vol. 122, pp. 161-174.

* cited by examiner

ANALYTIC METHOD AND KIT FOR DIAGNOSING ALCOHOL USE DISORDERS

TECHNICAL FIELD

The present invention relates to an analytical method for providing information necessary for a diagnosis of alcohol use disorder and a kit for a diagnosis of alcohol use disorder.

BACKGROUND ART

Alcohol is a prominent risk factor that contributes to the onset of various diseases and alcohol use disorder is a very important field for disease prevention and health care. According to the results of the epidemiological survey on mental illness by the Ministry of Health and Welfare in 2016, it is estimated that the annual prevalence of among alcohol-using adults over 18 years of age was 12.2%; and the socio-economic costs according to alcohol consumption, such as disease treatment expenses, losses of productivity and losses due to death, and property damages due to accidents, are about 20 trillion won, which is about 2.9% of GDP. In addition, the number of alcohol-related deaths in 2015 alone was 4,746, with an average of 13 deaths per day due to alcohol.

Alcohol use disorder refers to maladaptive disorders caused by excessive alcohol use (DSM 5, 2013), which combines alcohol dependence and abuse of the past DSM-IV (1994) into one diagnostic criterion. Alcohol use disorder is a medical diagnosis that is made when patients experience pain and harm from alcohol or when the disability therefrom persists. It is a disease in which a thirst for alcohol appears to the extent that it is difficult to think about anything else until the start of drinking.

Alcohol use disorder is caused by multiple factors and has a variety of clinical features. When environmental or genetic stimulus is received, almost all tissues show a stress response, which has a direct correlation with alcohol consumption. In case of excessive or binge drinking for a long time, the alcohol itself acts directly on the tissues associated in the stress response to increase the secretion of proteins including hormones, which intensifies the stress. There have been reported many studies suggesting that psychological stress can decrease various immune functions and increase susceptibility to physical diseases (Levy 1974; Herberman, 1982). Consistent alcohol drinking significantly lowers the amount of all types of white blood cells and reduces the production of immunoprotein antibodies. As a result, alcoholic over-drinking people have much lower immune function than normal people. Thus, they are much more likely to get external bacterial or viral diseases, and are also accompanied or caused by psychiatric disorders such as anxiety disorders, mood disorders, and dementia. Patients having alcohol use disorder need diagnosis and treatment for physical problems as well as psychological factors. Although many studies have been conducted on the psychological factors of alcohol use disorder, there has not yet been reported a studies on biomarkers capable of diagnosing physiological changes in the psychological risk factors and treatment progresses of alcohol use disorder.

Biomarkers are a kind of markers that objectively distinguish normal or pathological conditions. Since biomarkers can predict the outcome of treatment, the role thereof in the modern medical field is very important. Among the various biomarkers observed in the human body, the biomarkers that can link the changes and progresses of psychological risk factors in the field of addiction have not yet been reported, and thus further researches are required.

DISCLOSURE

Technical Problem

The present inventors discovered proteins that are specifically expressed according to the changes in risk factors associated in psychological factors of patients having alcohol use disorder, from serums derived from the bloods of patients having alcohol use disorder. That is, the present inventors have found that certain stress associated proteins, i.e., JNK, p-JNK, and Elk-1 proteins, are specifically highly expressed in patients having alcohol use disorder. Therefore, detection of overexpression of these proteins can be used as a biomarker for diagnosing alcohol use disorder.

Accordingly, it is an object of the present invention to provide an analytical method for providing information necessary for a diagnosis of alcohol use disorder, using the JNK, p-JNK, and/or Elk-1 protein.

In addition, it is another object of the present invention to provide a kit for a diagnosis of alcohol use disorder, comprising a molecule capable of measuring the expression levels of the genes encoding the JNK, p-JNK, and/or Elk-1 protein.

Technical Solution

In accordance with an aspect of the present invention, there is provided an analytical method for providing information necessary for a diagnosis of alcohol use disorder, comprising measuring (i) an expression level of a gene encoding a JNK or p-JNK protein in a subject's sample, (ii) an expression level of a gene encoding a JNK or p-JNK protein and an expression level of a gene encoding the Elk-1 protein in a subject's sample, or (iii) expression levels of genes encoding JNK, p-JNK, and Elk-1 proteins in a subject's sample, respectively.

In the analytical method of the present invention, the subject's sample may be blood or urine. The measuring expression level(s) of gene(s) may be carried out by measuring an amount of mRNA or protein. In an embodiment, the measuring an amount of protein may be carried out by Western blotting. In another embodiment, the measuring an amount of mRNA may be carried out by RT-PCR or real-time PCR.

In accordance with another aspect of the present invention, there is provided a kit for a diagnosis of alcohol use disorder, comprising (i) a molecule capable of measuring an expression level of a gene encoding a JNK or p-JNK protein, (ii) a molecule capable of measuring an expression level of a gene encoding a JNK or p-JNK protein and a molecule capable of measuring an expression level of a gene encoding the Elk-1 protein, or (iii) molecules capable of measuring expression levels of genes encoding JNK, p-JNK, and Elk-1 proteins, respectively, wherein the molecule(s) is (are) an antibody, substrate, ligand, or cofactor, which specifically binds to the protein; or a primer having a complementary sequence specific to the gene encoding the protein.

In an embodiment, the molecule(s) may be labeled with a detectable label. In another embodiment, the kit may be in the form of a microarray in which the primer is immobilized on a substrate.

Advantageous Effects

It has been found by the present invention that certain stress associated proteins, i.e., JNK, p-JNK, and Elk-1, are specifically highly expressed in patients having alcohol use disorder. Therefore, the analytical method and kit according to the present invention can be usefully applied for diagnosing alcohol use disorder and can effectively overcome the limitation of diagnosing alcohol use disorder through psychological behavioral factors.

BEST MODE

Figure 1:
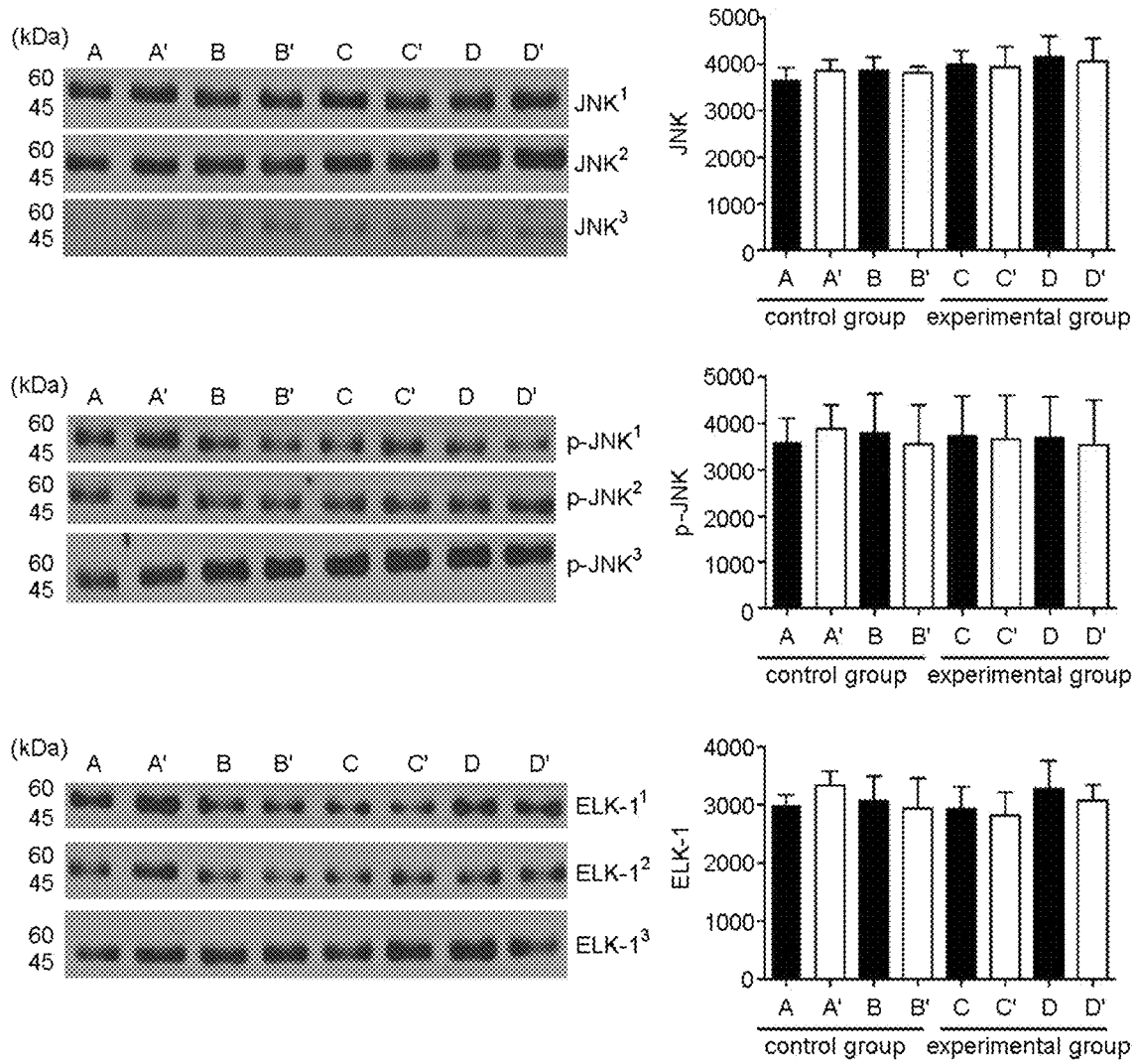
FIG. 1 shows the results of repeated experiments of Western blotting for proteins the bloods derived from two patients randomly selected from the control group and the experimental group.
   Control group before: A, B
   Control group after: A', B'
   Experimental group before: C, D
   Experimental group after: C', D'

As used herein, "alcohol use disorder (AUD)" refers to the disorder according to DSM 5 (the 5th edition of the Diagnostic and Statistical Manual of Mental Disorders) published in May 2013 by the American Psychiatric Association. According to the DSM-5 criteria, when at least two of the following items appear during the last 12 months according to a problematic alcohol use pattern that causes clinically significant damage or pain, it is diagnosed as alcohol use disorder.
1. Alcohol is often taken in larger amounts or over a longer period than was intended.
2. There is a persistent desire or unsuccessful efforts to cut down or control alcohol use.
3. A great deal of time is spent in activities necessary to obtain alcohol, use alcohol, or recover from its effects.
4. Craving, or a strong desire or urge to use alcohol.
5. Recurrent alcohol use resulting in a failure to fulfill major role obligations at work, school, or home.
6. Continued alcohol use despite having persistent or recurrent social or interpersonal problems caused or exacerbated by the effects of alcohol.
7. Important social, occupational, or recreational activities are given up or reduced because of alcohol use.
8. Recurrent alcohol use in situations in which it is physically hazardous.
9. Alcohol use is continued despite knowledge of having a persistent or recurrent physical or psychological problem that is likely to have been caused or exacerbated by alcohol.
10. Tolerance, as defined by either of the following:
   a. A need for markedly increased amounts of alcohol to achieve intoxication or desired effect, or
   b. A markedly diminished effect with continued use of the same amount of alcohol.
11. Withdrawal, as manifested by either of the following:
   a. The characteristic withdrawal syndrome for alcohol (tremors, insomnia, night sweats, nausea or vomiting, visual hallucinations, hallucinations, anxiety, etc.).
   b. Alcohol (or a closely related substance, such as a benzodiazepine) is taken to relieve or avoid withdrawal symptoms.

Therefore, in the present specification, the term 'alcohol use disorder (AUD)' means the disorders including all of alcohol dependence, abuse, and addiction.

In order to discover a serum biomarker that responds to the changes in psychological risk factors of alcohol use disorder, the present inventors determined the protein concentrations in each serum by the Bradford method and then analyzed differences in expression of the proteins associated with psychological risk factors before and after treatment, by the Western blotting method. The present inventors have found that certain stress-associated proteins, i.e., JNK, p-JNK, and Elk-1 proteins, are specifically overexpressed in patients having alcohol use disorder. Therefore, detecting overexpression of any one of the proteins or the proteins in a subject's sample can be usefully used to diagnose alcohol use disorder, and the proteins can be used as a biomarker for diagnosing alcohol use disorder.

In an aspect, the present invention provides an analytical method for providing information necessary for a diagnosis of alcohol use disorder, comprising measuring an expression level of a gene encoding a JNK or p-JNK protein in a subject's sample. In said analytical method, when the expression level of the gene encoding a JNK or p-JNK protein is significantly higher than that of a normal person (e.g., about 1.3 times or more, preferably about 1.5 times or more), the subject may be as a patient having alcohol use disorder.

C-Jun N-terminal kinase (JNK) is known to be responsive to stress stimuli, such as cytokines, ultraviolet irradiation, heat shock, and osmotic shock (Ip, Y. T., Davis, R. J., Signal transduction by the c-Jun N-terminal kinase (JNK)—from inflammation to development. *Current Opinion in Cell Biology*. 1998; 10(2):205-219). p-JNK refers to phosphorylated JNK. JNK plays an important role in the development of several diseases such as diabetes, neurodegenerative diseases and liver disease (Bogoyevitch, M. A., Ngoei, K. R. W., Zhao, T. T., Yeap, Y. Y. C., Ng, D. C. H. c-Jun N-terminal kinase (JNK) signaling: Recent advances and challenges. Biochimica et Biophysica Acta (BBA)—Proteins and Proteomics. 2010; 1804(3):463-475) and is activated by inflammatory signals, changes in reactive oxygen species, ultraviolet, protein synthesis inhibitors, and various stress stimuli (Vlahopoulos, S., Zoumpourlis, V. C. JNK: a key modulator of intracellular signaling. Biochemistry Moscow. 2004; 69(8):844-854). The NCBI accession number of the JNK protein is P45984, and the NCBI accession number of the mRNA encoding the same is NM_001278547, NM_002750, NM_139049, NM_139046, NM_001323331, NM_001323330, NM_001323329, NM_001323328, NM_001323327, NM_001323326, NM_001323325, NM_001323324, NM_001323323, NM_001323322, NM_001323321, NM_001323320, NM_001323302, NM_001278548, and so on. And, the NCBI accession number of the p-JNK protein is P45983, and the NCBI accession number of the mRNA encoding the same is XM_005265940, XM_006714891, XM_017009638, XM_017009639, XM_017009640, XM_017009642, NM_001135044, NM_002752, NM_139068, NM_139069, NM_139070, XM_017009641, XM_017009643, NM_001308244, and so on.

When the overexpression of JNK and/or p-JNK is detected in combination with the overexpression of Elk-1, it is possible to more efficiently diagnose alcohol use disorders. ETS transcription factor (Elk-1) is a transcription factor that directly regulates early gene (IEG) expression through a serum response element (SRE) DNA consensus site. Subhash C. Pandey et al. have suggested that the anxiolytic effects of acute ethanol in alcohol intoxication are associated with increased phosphorylation of Elk-1 and the anxiogenic effects of withdrawal symptoms following prolonged ethanol exposure are associated with decreased phosphorylation of Elk-1 (Subhash C. Pandey et al., Effector Immediate-Early Gene Arc in the Amygdala Plays a Critical Role in Alcoholism, *The Journal of Neuroscience*, Mar. 5, 2008, 28(10): 2589-2600). There have been known a variety of isoforms of Elk-1, and the term 'Elk-1 protein' herein includes all of the Elk-1 isoforms. The NCBI accession numbers of the Elk-1 isoforms (and the genes encoding the same) are XM_017029339, NM_001114123, NM_001257168, and NM_005229.

In another aspect, the present invention provides an analytical method for providing information necessary for a diagnosis of alcohol use disorder, comprising measuring an expression level of a gene encoding a JNK or p-JNK protein and an expression level of a gene encoding an Elk-1 protein in a subject's sample. In said analytical method, when the expression level of the gene encoding a JNK or p-JNK protein and the expression level of the gene encoding an Elk-1 protein are respectively significantly higher than those of a normal person (e.g., about 1.3 times or more, preferably about 1.5 times or more), the subject may be as a patient having alcohol use disorder.

In still another aspect, the present invention provides an analytical method for providing information necessary for a diagnosis of alcohol use disorder, comprising measuring expression levels of genes encoding JNK, p-JNK, and Elk-1 proteins in a subject's sample, respectively. In said analytical method, when the expression levels of each gene encoding JNK, p-JNK, and Elk-1 proteins are significantly higher than those of a normal person (e.g., about 1.3 times or more, preferably about 1.5 times or more), the subject may be as a patient having alcohol use disorder.

In the analytical method of the present invention, the subject's sample refers to a sample externally discharged from the human body, including e.g., blood, urine, etc. externally discharged from the human body.

The analytical method of the present invention comprises measuring an expression level of a gene encoding a JNK or p-JNK protein; or an expression level of a gene encoding a JNK or p-JNK protein and an expression level of a gene encoding an Elk-1 protein; or expression levels of genes encoding JNK, p-JNK, and Elk-1 proteins, respectively. Each gene sequence encoding the JNK, p-JNK, and Elk-1 proteins may be a gene known in GenBank and the like as described above.

The measuring gene expression level(s) may be carried out by measuring a level(s) of mRNA of the gene(s) or a level(s) of the protein(s), according to a method conventionally used in the field of biotechnology. The measuring an amount of protein(s) may be carried out by e.g., Western blotting. In case of measuring the amount of protein(s) by the Western blotting method, when the expression level of the measured protein(s) is significantly higher than that of a normal person (e.g., about 1.3 times or more, preferably about 1.5 times or more), the subject may be as a patient having alcohol use disorder. In addition, the measuring an amount of mRNA of gene(s) encoding the protein(s) may be carried out by e.g., reverse transcription-PCR (RT-PCR) or real-time PCR.

The present invention also provides a kit for a diagnosis of alcohol use disorder, comprising (i) a molecule capable of measuring an expression level of a gene encoding a JNK or p-JNK protein, (ii) a molecule capable of measuring an expression level of a gene encoding a JNK or p-JNK protein and a molecule capable of measuring an expression level of a gene encoding the Elk-1 protein, or (iii) molecules capable of measuring expression levels of genes encoding JNK, p-JNK, and Elk-1 proteins, respectively, wherein the molecule(s) is (are) an antibody, substrate, ligand, or cofactor, which specifically binds to the protein; or a primer having a complementary sequence specific to the gene encoding the protein.

The molecule(s) capable of measuring an expression level of a gene may be an antibody, substrate, ligand, or cofactor, which specifically binds to the protein(s); or a primer having a complementary sequence specific to the gene encoding the protein.

The protein(s) may be used to prepare a polyclonal antibody or a monoclonal antibody and a diagnostic kit comprising the antibody may be also prepared, according to a method conventionally used in the field of biotechnology. And, since the function of the protein(s) has been revealed, the kit of the present invention may be prepared to comprise a substrate, a ligand, or a cofactor thereto. In addition, a primer having a complementary sequence specific to the gene encoding the protein(s) may be prepared and a diagnostic kit comprising the primer may be also prepared, according to a method conventionally used in the field of biotechnology.

In the diagnostic kit of the present invention, a molecule capable of measuring an expression level of a gene encoding the protein(s) may be labeled with a detectable label (e.g., a chromophore, etc.). And, the diagnostic kit of the present invention may be in the form of a microarray, e.g., in the form of a chip such as a DNA chip or a protein chip, in which the primer is immobilized on a substrate.

Hereinafter, the present invention will be described more specifically by the following examples. However, the following examples are provided only for illustrations and thus the present invention is not limited to or by them.

EXAMPLES

1. Methods (1) Patient Recruitment

Patients diagnosed with alcohol use disorder were randomly classified into a control group and an experimental group. Among the 20-65-year-old adults admitted to the psychiatry department of KARF St. Mary's Hospital in Ilsan, Gyeonggi-do, Korea, 35 participants who met the criteria of the study participants were enrolled. The study began with 55 participants after the initial assessment, but was ultimately conducted with 35 participants after 20 people dropped out due to personal reasons (discharge or suspension due to relapse). Each blood was collected and then centrifuged at 1,500 g for 15 minutes to obtain the serum for using the experiments.

(2) Analysis of Stress-Associated Proteins in the Serum Using Western Blotting

In the patients having alcohol use disorder, the measurement was performed using the serums collected from the control group who psychological support had not been provided and the serums collected from the experimental group who psychological support had been provided. After measuring the protein concentrations in each serum using the Bradford method, Western blotting was carried out with anti-JNK, anti-p-JNK, and anti-Elk-1 antibodies to analyze expression levels of the proteins. First, the total proteins in each serum were quantified by the Bradford method, and then each 20 µg thereof was subject to electrophoresis at 120

Volt for 1.5 hours on SDS-PAGE (Sodium Dodecyl Sulfate-Polyacrylamide Gel Electrophoresis). The protein in the gel was then transferred to a nitrocellulose membrane (PVDF, Bio-Rad, CA, USA) at 120 Volt for 1 hour. We prepared a washing buffer consisting of 10 mM Tris-HCl (pH 7.5) (2 M stock 5 ml), 100 mM NaCl (5 M stock 20 ml), 1 ml of 0.1% Tween 20, and 976 ml of distilled water. The membrane was added to a 5% blocking buffer prepared by dissolving 2.5 mg of nonfat milk in 50 ml of the washing solution and then reacted at room temperature for 30 minutes.

Thereafter, the membrane was reacted overnight at 4° C. with the diluted (1:1,000) anti-JNK, anti-p-JNK, or anti-Elk-1 antibody (polyclonal antibody, primary antibody). The resulting membrane was washed with the washing solution, reacted for 1 hour with the diluted (1:10,000) HRP-labeled polyclonal goat anti-rabbit IgG (secondary antibody), and then washed again with the washing solution. Luminescence reaction thereto was carried out with ECL (enhanced chemiluminescence kit, Young In Frontier, Seoul, Korea), followed by developing on an X-ray film.

2. Results and Discussion

Figure 2:
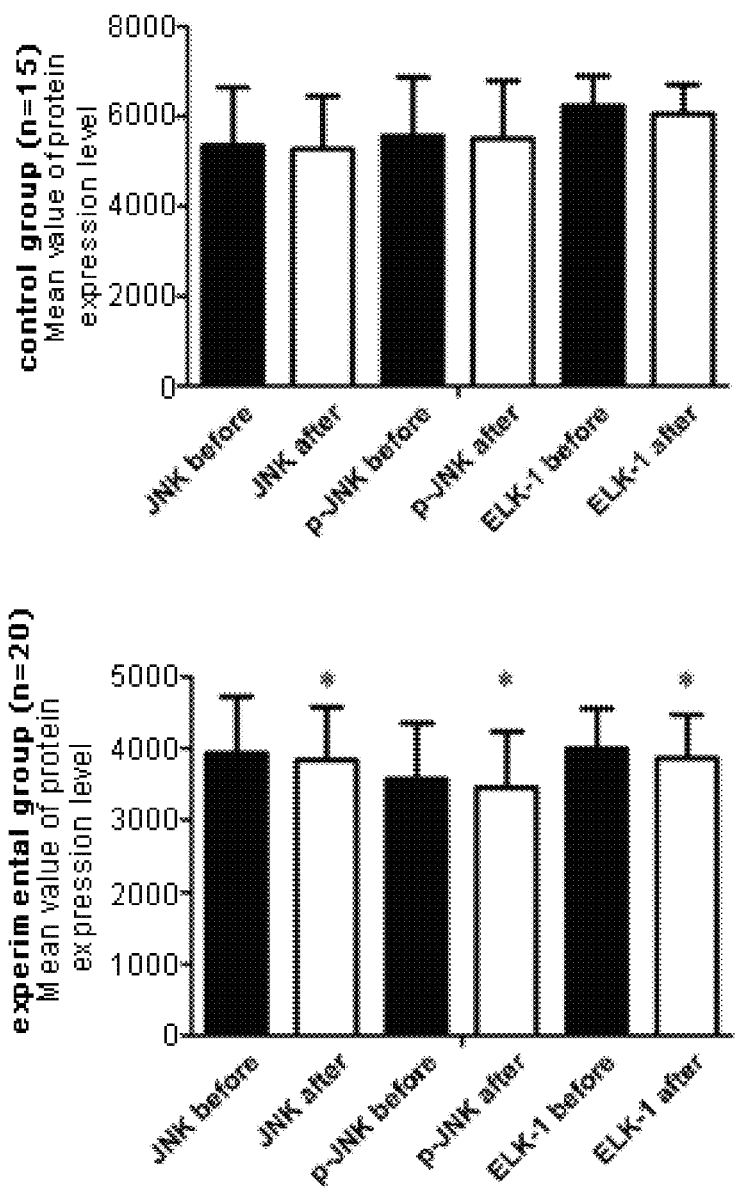
FIG. 2 shows the statistical t-test analysis results on the Western blotting results of JNK, p-JNK and Elk-1 in the control group (n=15) and the experimental group (n=20). *p<0.05 was considered statistically significant.

Out of the total 35 participants, 2 participants in the control group and 2 participants in the experimental group were randomly selected. The proteins in each blood derived from the 4 participants were quantified and the results obtained according to the repeated experiments by Western blotting were statistically analyzed. The results thereof are shown in FIG. 1. From the results of FIG. 1, the expressions of the JNK, p-JNK, and Elk-1 antibodies in the experimental group were decreased. Based on these results, the serums of all participants were analyzed. As the results thereof, the experimental group showed statistically significant changes in the expressions of JNK, p-JNK, and Elk-1, compared to the control group (FIG. 2): JNK (t=3.174, p=0.005), p-JNK (t=2.450, p=0.024), Elk-1 (t=2.933, p=0.009).

From the above results, it was verified that certain proteins, i.e., JNK, p-JNK, and Elk-1, are specifically expressed in the serum of patients having alcohol use disorder. Subhash C. Pandey et al. have suggested that the anxiolytic effects of acute ethanol in alcohol intoxication are associated with increased phosphorylation of Elk-1 and the anxiogenic effects of withdrawal symptoms following prolonged ethanol exposure are associated with decreased phosphorylation of Elk-1 (Subhash C. Pandey et al., Effector Immediate-Early Gene Arc in the Amygdala Plays a Critical Role in Alcoholism, *The Journal of Neuroscience*, Mar. 5, 2008, 28 (10): 2589-2600). It is confirmed by this study that Elk-1 is associated with alcohol use disorder in humans, thereby being able to be used as a biomarker. In particular, there is no previous study suggesting that JNK and p-JNK are associated with alcohol use disorder and thus can be used as a serum biomarker. Therefore, detecting overexpression of JNK and/or p-JNK or detecting overexpression of JNK and/or p-JNK in combination with overexpression of Elk-1 makes it possible to diagnose alcohol use disorder. In addition, these proteins can be used as a serum biomarker which responds to psychological risk factors of alcohol use disorders.

The invention claimed is:

1. An analytical method for providing information necessary for a diagnosis and treatment of alcohol use disorder in a subject in need thereof, comprising
   (a) measuring expression levels of JNK, p-JNK, and Elk-1 proteins in a serum sample of a subject,
   (b) diagnosing the subject as having alcohol use disorder, wherein the diagnosis is based on a finding that the expression levels are 1.3 or more times higher in the subject compared to those of a person without alcohol use disorder, and
   (c) providing the subject having alcohol use disorder with psychological support,
   wherein the measuring is performed with antibodies capable of measuring the expression levels of JNK, p-JNK, and Elk-1 proteins.

\* \* \* \* \*